United States Patent [19]

Smith et al.

[11] Patent Number: 5,219,886
[45] Date of Patent: Jun. 15, 1993

[54] MERCAPTO-ACYLAMINO ACIDS

[75] Inventors: Elizabeth M. Smith, Verona; Philip M. DeCapite, Bloomfield; Bernard R. Neustadt, West Orange, all of N.J.

[73] Assignee: Schering Corporation, Kenilworth, N.J.

[21] Appl. No.: 768,647

[22] PCT Filed: Apr. 6, 1990

[86] PCT No.: PCT/US90/01787
§ 371 Date: Oct. 1, 1991
§ 102(e) Date: Oct. 1, 1991

Related U.S. Application Data

[63] Continuation-in-part of Ser. No. 335,264, Apr. 10, 1989, abandoned.

[51] Int. Cl.⁵ .................. A61K 31/258; C07C 321/10
[52] U.S. Cl. ..................................... 514/533; 560/16;
560/147; 560/153; 562/426; 549/71; 549/468;
549/469; 549/484; 549/486; 549/58; 549/76;
549/77; 549/493; 549/496; 546/335; 514/538;
514/539; 514/560; 514/563
[58] Field of Search ............... 560/16, 147, 153;
562/426; 514/538, 539, 562, 563, 443, 469, 471,
357, 558, 559, 535, 547, 513, 448, 438, 616;
549/76, 77, 493, 496, 58, 484, 486, 71, 468, 464;
546/335; 564/154; 558/254

[56] References Cited

U.S. PATENT DOCUMENTS

| | | | |
|---|---|---|---|
| 4,053,651 | 10/1977 | Ondetti et al. | 424/319 |
| 4,105,776 | 8/1978 | Ondetti et al. | 424/274 |
| 4,228,077 | 10/1980 | Ondetti et al. | 260/326.14 T |
| 4,256,761 | 3/1981 | Suh et al. | 424/282 |
| 4,329,495 | 5/1982 | Bindra | 562/426 |
| 4,344,949 | 8/1982 | Hoefle et al. | 424/258 |
| 4,350,704 | 9/1982 | Hoefle et al. | 424/274 |
| 4,374,829 | 2/1983 | Harris et al. | 424/177 |
| 4,374,847 | 2/1983 | Gruenfeld | 424/274 |
| 4,401,677 | 8/1983 | Greenburg et al. | 424/317 |
| 4,410,520 | 10/1983 | Watthey | 424/244 |
| 4,462,943 | 7/1984 | Petrillo et al. | 548/533 |
| 4,468,519 | 8/1984 | Krapcho | 548/409 |
| 4,470,972 | 9/1984 | Gold et al. | 424/177 |
| 4,470,973 | 9/1984 | Natarajan et al. | 424/177 |
| 4,500,467 | 2/1985 | Kubinyi et al. | 514/2 |
| 4,508,729 | 4/1985 | Vincent et al. | 514/419 |
| 4,512,924 | 4/1985 | Attwood et al. | 544/61 |
| 4,513,009 | 4/1985 | Roques et al. | 514/513 |

(List continued on next page.)

Primary Examiner—Richard L. Raymond
Assistant Examiner—Mark W. Russell
Attorney, Agent, or Firm—Anita W. Magatti; Eric S. Dicker

[57] ABSTRACT

Novel mercapto-acylamino acids of the formula

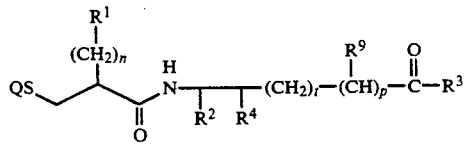

wherein
Q is hydrogen or R⁷CO—;
R¹ is lower alkyl, cyclolower alkyl, aryl or heteroaryl;
R² is hydrogen; lower alkyl; cyclolower alkyl; lower alkyl substituted with hydroxy, lower alkoxy, mercapto, lower alkylthio, aryl or heteroaryl; aryl; or heteroaryl;
R³ is —OR⁵ or —NR⁵R⁶;
R⁴ and R⁹ are independently —(CH₂)$_q$R⁸, provided that when R⁴ and R⁹ are both hydrogen, R² is biphenylyl, phenoxyphenyl, phenylthiophenyl, naphthyl, heteroaryl, or lower alkyl substituted with hydroxy, lower alkoxy, mercapto or lower alkylthio;
R⁵ and R⁶ are independently selected from the group consisting of hydrogen, lower alkyl, hydroxy lower alkyl, lower alkoxy lower alkyl and aryl lower alkyl, or R⁵ and R⁶ together with the nitrogen to which they are attached form a 5-7 membered ring;
R⁷ is hydrogen, lower alkyl or aryl;
R⁸ is hydrogen, hydroxy, lower alkoxy, mercapto, lower alkylthio, aryl or heteroaryl;
n is 1 or 2;
p is 0 or 1;
q is 0, 1 or 2; and
t is 0 or 1; and the pharmaceutically acceptable salts thereof useful in the treatment of cardiovascular disorders and pain conditions and combinations of mercapto-acrylamino acids and atrial natriuretic factors or angiotensin converting enzyme inhibitors useful for treating cardiovascular disorders are disclosed.

10 Claims, No Drawings

U.S. PATENT DOCUMENTS

| | | | |
|---|---|---|---|
| 4,555,506 | 11/1985 | Karanewsky et al. | 514/91 |
| 4,719,231 | 1/1988 | Umezawa et al. | 514/513 |
| 4,740,499 | 4/1988 | Olins | 514/13 |
| 4,749,688 | 6/1988 | Haslanger et al. | 514/19 |
| 4,774,256 | 9/1988 | Delaney et al. | 514/513 |
| 4,801,609 | 1/1989 | Haslanger et al. | 514/19 |
| 4,879,309 | 11/1989 | Doll et al. | 514/513 |
| 4,929,641 | 5/1990 | Haslanger et al. | 514/513 |

FOREIGN PATENT DOCUMENTS

| | | |
|---|---|---|
| 38046 | 10/1981 | European Pat. Off. |
| 46953 | 3/1982 | European Pat. Off. |
| 50800 | 5/1982 | European Pat. Off. |
| 79022 | 5/1983 | European Pat. Off. |
| 79522 | 6/1983 | European Pat. Off. |
| 8400670 | 9/1985 | South Africa |
| 2095682 | 10/1982 | United Kingdom |
| 2207351 | 2/1989 | United Kingdom |

OTHER PUBLICATIONS

Needleman et al., *N. Eng. J. Med.*, 314, 13 (1986) pp. 828–834.

Cantin, et al., *Sci. Amer.*, 254 (1986) pp. 76–81.

Wyvratt, et al., *Med. Res. Rev.*, 5 (1985) pp. 483–531.

MERCAPTO-ACYLAMINO ACIDS

The present application is the United States national application corresponding to International Application No. PCT/US90/01787, filed Apr. 6, 1990 and designating the United States, which PCT application is, in turn, a continuation-in-part of U.S. application Ser. No. 335,264, filed Apr. 10, 1989, now abandoned the benefit of which application is claimed pursuant to the provisions of 36 U.S.C.§§ 120, 363 and 365 (c).

BACKGROUND OF THE INVENTION

The present invention relates to mercapto-acylamino acids useful in the treatment of cardiovascular disorders and pain conditions.

Cardiovascular disorders which may be treated with compounds of the present invention include hypertension, congestive heart failure, edema and renal insufficiency.

Human hypertension represents a disease of multiple etiologies. Included among these is a sodium and volume dependent low renin form of hypertension. Drugs that act to control one aspect of hypertension will not necessarily be effective in controlling another.

Enkephalin is a natural opiate receptor agonist which is known to produce a profound analgesia when injected into the brain ventricle of rats. It is also known in the art that enkephalin is acted upon by a group of enzymes known generically as enkephalinases, which are also naturally occurring, and is inactivated thereby.

A variety of mercaptoacylamino acids are known as enkephalinase inhibitors useful as analgesics and in the treatment of hypertension. Most are alpha amino acids, however European Patent Application 136,883, published Apr. 10, 1985, and U.S. Pat. No. 4,774,256 disclose, inter alia, compounds of the formula

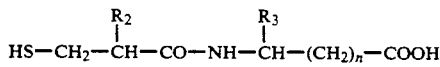

wherein n is 1–15 and $R_2$ and $R_3$ are various aryl, arylalkyl and heteroarylalkyl groups. The compounds are disclosed as having enkephalinase inhibiting activity.

It has recently been discovered that the heart secretes a series of peptide hormones called atrial natriuretic factors (ANF) which help to regulate blood pressure, blood volume and the excretion of water, sodium and potassium. ANF were found to produce a short-term reduction in blood pressure and to be useful in the treatment of congestive heart failure. See P. Needleman et al, "Atriopeptin: A Cardiac Hormone Intimately Involved in Fluid, Electrolyte and Blood-Pressure Homeostasis", *N. Engl. J. Med.*, 314, 13 (1986) pp. 828–834, and M. Cantin et al in "The Heart as an Endocrine Gland", *Scientific American*, 254 (1986) pg. 7681.

A class of drugs known to be effective in treating some types of hypertension is ACE inhibitors, which compounds are useful in blocking the rise in blood pressure caused by increases in vascular resistance and fluid volume due to the formation of angiotension II from angiotensin I. For a review of ACE inhibitors, see M. Wyvratt and A. Patchett, "Recent Developments in the Design of Angiotensin Converting Enzyme Inhibitors" in *Med. Res. Rev.* Vol. 5, No. 4 (1985) pp. 483–531.

SUMMARY OF THE INVENTION

Novel compounds of the present invention are represented by the formula

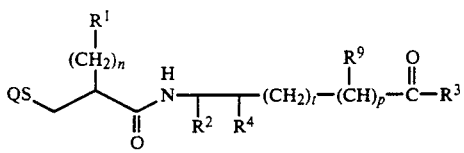

wherein
Q is hydrogen or $R^7CO—$;
$R^1$ is lower alkyl, cyclolower alkyl, aryl or heteroaryl;
$R^2$ is hydrogen; lower alkyl; cyclolower alkyl; lower alkyl substituted with hydroxy, lower alkoxy, mercapto, lower alkylthio, aryl or heteroaryl; aryl; or heteroaryl;
$R^3$ is $—OR^5$ or $—NR^5R^6$;
$R^4$ and $R^9$ are independently $—(CH_2)_qR^8$, provided that when $R^4$ and $R^9$ are both hydrogen, $R^2$ is biphenylyl, phenoxyphenyl, phenylthiophenyl, naphthyl, heteroaryl, or lower alkyl substituted with hydroxy, lower alkoxy, mercapto or lower alkylthio;
$R^5$ and $R^6$ are independently selected from the group consisting of hydrogen, lower alkyl, hydroxy lower alkyl, lower alkoxy lower alkyl and aryl lower alkyl, or $R^5$ and $R^6$ together with the nitrogen to which they are attached form a 5–7 membered ring;
$R^7$ is hydrogen, lower alkyl or aryl;
$R^8$ is hydrogen, hydroxy, lower alkoxy, mercapto, lower alkylthio, aryl or heteroaryl;
n is 1 or 2;
p is 0 or 1;
q is 0, 1 or 2; and
t is 0 or 1;
and the pharmaceutically acceptable salts thereof.

A preferred group of compounds of the present invention is that wherein t is zero, with compounds wherein p and t are both zero being more preferred. Another group of preferred compounds is that wherein $R^4$ is hydrogen, hydroxy, methoxy, phenyl or benzyl. Still another preferred group is that wherein $R^2$ is hydrogen or thienyl. Preferred amino acid portions of the compounds of formula I (i.e. the portion $—NH—CH(R^2)—CH(R^4)—(CH_2)_t—(CHR^9)_p—COR^3$) are those wherein p and t are each 0, $R^2$ is hydrogen and $R^4$ is hydroxy or methoxy (e.g. isoserine or O-methyl isoserine); those wherein t is 1, p is 0, $R^2$ is hydrogen and $R^4$ is hydroxy (e.g. homo-isoserine); those wherein p and t are each 0, $R^2$ is thienyl and $R^4$ is hydrogen (e.g. β-thienyl-β-alanine); and those wherein p and t are each 0, $R^2$ is hydrogen and $R^4$ is phenyl or benzyl.

Other preferred compounds of formula I are those wherein Q is hydrogen or acyl. Still other preferred compounds are those wherein $R^1$ is phenyl or lower alkyl-substituted phenyl, for example tolyl. Yet another preferred group of compounds is that wherein $R^3$ is hydroxy or lower alkoxy. A preferred value for n is 1.

Especially preferred compounds of formula I are those wherein Q is hydrogen or acyl; $R^1$ is phenyl or tolyl; n is 1; $R^2$ is hydrogen or thienyl; $R^4$ is hydrogen, hydroxy, methoxy, phenyl or benzyl; p is 0; and $R^3$ is hydroxy or lower alkoxy.

Examples of especially preferred compounds of formula I wherein n is 1 and p is zero are shown in the following Table 1:

TABLE 1

| Compound | t | Q | R¹ | R² | R³ | R⁴ |
|---|---|---|---|---|---|---|
| a | 0 | H | Ph | H | OH | OH |
| b | 0 | H | Ph | H | OH | Ph |
| c | 0 | Ac | Ph | 3-Thienyl | OMe | H |
| d | 0 | H | Ph | 3-Thienyl | OH | H |
| e | 1 | Ac | Ph | H | OMe | OH |
| f | 0 | Ac | o-Tol | H | OEt | OH |
| g | 0 | Ac | o-Tol | H | OEt | Benzyl |
| h | 1 | H | Ph | H | OH | OH |
| i | 0 | H | o-Tol | H | OH | OH |
| j | 0 | H | o-Tol | H | OH | OMe |

The invention also relates to the treatment of cardiovascular diseases with a combination of a mercapto-acylamino acid of the present invention and an atrial natriuretic factor (ANF) and with a combination of a mercapto-acylamino acid of the present invention and an angiotensin converting enzyme (ACE) inhibitor.

Other aspects of the invention relate to pharmaceutical compositions comprising a mercapto-acylamino acid of this invention, alone or in combination with an ANF or an ACE inhibitor, and to methods of treatment of cardiovascular diseases comprising administering a mercapto-acylamino acid of this invention, alone or in combination with an ANF or an ACE inhibitor, to a mammal in need of such treatment.

Still another aspect of the invention relates to a method of treating pain conditions by administering a mercapto-acylamino acid of this invention, thereby inhibiting the action of enkephalinase in a mammal and eliciting an analgesic effect. Analgesic pharmaceutical compositions comprising said mercapto-acylamino compounds are also contemplated.

DETAILED DESCRIPTION

As used herein, the term "lower alkyl" means straight or branched alkyl chains of 1 to 6 carbon atoms, and "lower alkoxy" similarly refers to alkoxy groups having 1 to 6 carbon atoms. Cyclolower alkyl means cyclic alkyl groups of 3 to 6 carbon atoms.

"Aryl" means mono-cyclic or fused ring bicyclic carbocyclic aromatic groups having 6 to 10 ring members and "heteroaryl" means mono-cyclic or fused ring bicyclic aromatic groups having 5–10 ring members wherein 1-2 ring members are independently nitrogen, oxygen or sulfur, wherein the carbon ring members of the aryl and heteroaryl groups are substituted by zero to three substituents selected from the group consisting of lower alkyl, hydroxy, halogeno, lower alkoxy, trifluoromethyl, phenyl, phenoxy or phenylthio. Examples of carbocyclic aryl groups are phenyl, α-naphthyl and β-naphthyl, and examples of heterocyclic aryl groups are furyl, thienyl, pyrrolyl, benzofuryl, benzothienyl, indolyl and pyridyl. All positional isomers, e.g. 2-pyridyl, 3-pyridyl, are contemplated.

"Halo" refers to fluorine, chlorine, bromine or iodine radicals.

Certain compounds of the invention are acidic e.g., those compounds which possess a carboxyl group. These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Compounds of formula I have at least one asymmetrical carbon atom and therefore include various stereoisomers. The invention includes all such isomers both in pure form and in admixture, including reacemic mixtures.

An aspect of the present invention described above relates to the combination of a compound of formula I with an ANF. As indicated by Needleman et al., a number of ANF have been isolated so far, all having the same core sequence of 17 amino acids within a cysteine disulfide bridge, but having different N-termini lengths. These peptides represent N-terminal truncated fragments (21–48 amino acids) of a common preprohormone (151 and 152 amino acids for man and rats, respectively). Human, porcine and bovine carboxy-terminal 28-amino acid peptides are identical and differ from similar peptides in rats and mice in that the former contain a methionine group at position 12 while the latter contain iscleucine. Various synthetic analogs of naturally occuring ANF's also have been found to have comparable biological activity. Examples of ANFs contemplated for use in this invention are α human AP 21 (atriopeptin I), α human AP 28, α human AP 23 (atriopeptin II or APII), α human AP 24, α human AP 25, α human AP 26, α human AP 33, and the corresponding rat sequence of each of the above wherein Met 12 is Ile. See Table II for a comparison of the peptides.

TABLE II

| ROMAN PEPTIDE | Sequence |
|---|---|
| AP 33 | Leu Ala Gly Pro Arg Ser Leu Arg Arg Ser Ser Cys—S Phe Gly Gly Arg Met* Asp Arg Ile Gly Ala Gln Ser Gly Leu Gly Cys—S Asn Ser Phe Arg Tyr |
| AP 28 | .......... Ser .......... Arg .................................................................. Tyr |
| AP 26 | ........................ Arg .................................................................... Tyr |
| AP 25 | .................................. Arg .......................................................... Tyr |
| AP 24 | .................................. Ser .......................................................... Tyr |
| AP 23 | .................................. Ser .......................................................... Arg |
| AP 21 | .................................. Ser .......................................................... Ser |

*Ile is the rat peptide

Another aspect of the invention is the administration of a combination of an ACE inhibitor and a compound of formula I.

Examples of ACE inhibitors are those disclosed in the article by Wyvratt et al., cited above, and in the following U.S. patents: U.S. Pat. Nos. 4,105,776, 4,468,519, 4,555,506, 4,374,829, 4,462,943, 4,470,973, 4,470,972, 4,350,704, 4,256,761, 4,344,949, 4,508,729, 4,512,924, 4,410,520 and 4,374,847, all incorporated herein by reference; and the following foreign patents or published patent applications:

British Specification No. 2095682 published Oct. 6, 1982 discloses N-substituted-N-carboxyalkyl aminocarbonyl alkyl glycine derivatives which are said to be angiotensin converting enzyme inhibitors and have the formula

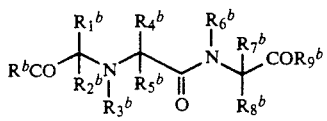

either (A) $R^b$ and $R_9^b$ are OH, 1-6C alkoxy, 2-6C alkenyloxy, di(1-6C alkyl)amino-(1-6C) alkoxy, 1-6C hydroxyalkoxy, acylamino-(1-6C)alkoxy, acyloxy-(1-6C)alkoxy, aryloxy, aryloxy-(1-6C)alkoxy, $NH_2$, mono- or di-(1-6C alkyl)amino, hydroxyamino or aryl-(1-6C)alkylamino;

$R_1^b$-$R_5^b$, $R_7^b$ and $R_8^b$ are 1-20C alkyl, 2-20C alkenyl, 2-20C alkynyl, aryl, aryl-(1-6C) alkyl having 7-12C or heterocyclyl-(1-6C)alkyl having 7-12C;

$R_6^b$ is cycloalkyl, polycycloalkyl, partly saturated cycloalkyl or polycycloalkyl, cycloalkyl-(1-6C)alkyl having 3-20C, 6-10C aryl, aryl-(1-6C)alkyl, aryl-(2-6C)alkenyl or aryl-(2-6C) alkynyl; or $R_2^b$ and $R_3^b$ together with the C and N atoms to which they are attached or $R_3^b$ and $R_5^b$ together with the N and C atoms to which they are attached form an N-heterocycle containing 3-5C or 2-4C and a S atom;

all alkyl, alkenyl and alkynyl are optionally substituted by OH, 1-6C alkoxy, thio(sic), 1-6C alkylthio, $NH_2$, mono-or di(1-6C alkyl)amino, halogen or $NO_2$;

all 'cycloalkyl' groups (including poly and partially unsaturated) are optionally substituted by halogen, 1-6C hydroxyalkyl, 1-6C alkoxy, amino-(1-6C alkyl)amino, di-(1-6C alkyl)amino, SH, 1-6C alkylthio, $NO_2$ or $CF_3$; and aryl groups are optionally substituted by OH, 1-6C alkoxy, $NH_2$, mono- or di-(1-6C alkyl) amino, SH, 1-6C alkylthio, 1-6C hydroxyalkyl, 1-6C aminoalkyl, 1-6C thioalkyl, $NO_2$, halogen, $CF_3$, $OCH_2O$, ureido or guanidino; or (B) $R^b$ and $R_9^b$ are H or 1-6C alkoxy;

$R_1^b$ and $R_2^b$ are H, 1-6C alkyl, aryl-(1-6C) alkyl having 7-12C or heterocyclyl-(1-6C) alkyl having 6-12C; $R_3^b$-$R_5^b$, $R_7^b$ and $R_8^b$ are H or 1-6C alkyl;

$R_6^b$ is cycloalkyl, polycycloalkyl, partly saturated cycloalkyl or polycycloalkyl, cycloalkyl-(1-6C) alkyl having 3-20C, aryl or aryl-(1-6C) alkyl; and aryl has 6-10C and is optionally substituted by 1-6C alkyl, 2-6C alkenyl, 2-6C alkynyl, OH, 1-6C alkoxy, $NH_2$, mono-or di-(1-6C alkyl) amino, SH, 1-6C alkylthio, 1-6C hydroxyalkyl, 1-6C aminoalkyl, 1-6C thioalkyl, $NO_2$, halogen, $CF_3$, $OCH_2O$, ureido or guanidino;

European Patent Application 0 050 800 published May 5, 1982 discloses carboxyalkyl dipeptides derivatives which are said to be angiotensin converting enzyme inhibitors and have the formula

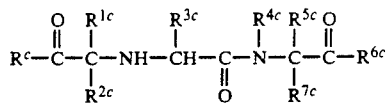

or a pharmaceutically acceptable salt thereof, wherein $R^c$ and $R^{6c}$ are the same or different and are hydroxy, lower alkoxy, lower alkenyloxy, dilower alkylamino lower alkoxy, acylamino lower alkoxy, acyloxy lower alkoxy, aryloxy, aryllower alkoxy, amino, lower alkylamino, dilower alkylamino, hydroxyamino, aryllower alkylamino, or substituted aryloxy or substituted aryllower alkoxy wherein the substituent is methyl, halo or methoxy; $R^{1c}$ is hydrogen, alkyl of from 1 to 10 carbon atoms, substituted lower alkyl wherein the substituent is hydroxy, lower alkoxy, aryloxy, substituted aryloxy, heteroaryloxy, substituted heteroaryloxy, amino, lower alkylamino, diloweralkylamino, acylamino, arylamino, substituted arylamino, guanidino, imidazolyl, indolyl, lower alkylthio, arylthio, substituted arylthio, carboxy, carbamoyl, lower alkoxy carbonyl, aryl, substituted aryl, aralkyloxy, substituted aralkyloxy, aralkylthio or substituted aralkylthio, wherein the aryl or heteroaryl portion of said substituted aryloxy, heteroaryloxy, arylamino, arylthio, aryl, aralkyloxy, aralkylthio group is substituted with a group selected from halo, lower alkyl, hydroxy, lower alkoxy, amino, aminomethyl, carboxyl, cyano, or sulfamoyl; $R^{2c}$ and $R^{7c}$ are the same or different and are hydrogen or lower alkyl; $R^{3c}$ is hydrogen, lower alkyl, phenyl lower alkyl, aminoethylphenyl lower alkyl, hydroxyphenyl lower alkyl, hydroxy lower alkyl, acylamino lower alkyl, amino lower alkyl, dimethylamino lower alkyl, guanidino lower alkyl, imidazolyl lower alkyl, indolyl lower alkyl, or lower alkyl thio lower alkyl; $R^{4c}$ and $R^{5c}$ are the same or different and are hydrogen, lower alkyl or $Z^c$, or $R^{4c}$ and $R^{5c}$ taken together form a group represented by $Q^c$, $U^c$, $V^c$, $Y^c$, $D^c$ or $E^c$, wherein;

$Z^c$ is

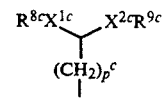

wherein $X^{1c}$ and $X^{2c}$ independent of each other are O, S or $CH_2$, $R^{8c}$ and R9c independent of each other are lower alkyl, lower alkenyl, lower alkynyl, cycloalkyl having 3 to 8 carbon atoms, hydroxy lower alkyl, or —$(CH_2)_n{}^c Ar^c$, wherein $n^c$ is 0, 1, 2 or 3 and $Ar^c$ is unsubstituted or substituted phenyl, furyl, thienyl or pyridyl, wherein said substituted phenyl, furyl, thienyl or pyridyl groups are substituted with at least one group that is independently selected from $C_1$ to $C_4$ alkyl, lower alkoxy, lower alkylthio, halo, $CF_3$ and hydroxy, or $R^{8c}$ and $R^{9c}$ taken together form a bridge $W^c$, wherein $W^c$ is a single bond or a methylene bridge or a substituted methylene bridge when at least one of $X^{1c}$ and $X^{2c}$ is methylene, or $W^c$ is an alkylene or substituted alkylene bridge having 2 or 3 carbon atoms, said substituted methylene bridge or said substituted alkylene bridge having one or two substituents selected from lower alkyl, aryl and aryl lower alkyl groups, and $p^c$ is 0, 1 or 2; with the proviso that at least one of $R^{4c}$ and $R^{5c}$ is $Z^c$, with the proviso that if $R^{4c}$ is $Z^c$ and $p^c$ is 0 then $X^{1c}$ and $X^{2c}$ must both be methylene, and with the proviso that if $X^{1c}$ and $X^{2c}$ are both methylene then $R^{8c}$ and $R^{9c}$ must form an alkylene bridge $W^c$;

$Q^c$ is

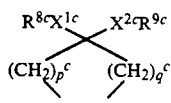

wherein $R^{8c}$, $R^{9c}$, $X^{1c}$ and $X^{2c}$ are as defined above, $p^c$ is 0, 1 or 2, $q^c$ is 0, 1 or 2, with the proviso that the sum of $p^c$ and $q^c$ must be 1, 2 or 3, with the proviso that if $p^c$ is 0 then $X^{1c}$ and $X^{2c}$ must be methylene, and with the proviso that if $X^{1c}$ and $X^{2c}$ are methylene then $R^{8c}$ and $R^{9c}$ taken together form a bridge $W^c$, wherein $W^c$ is as defined above;

$V^c$ is

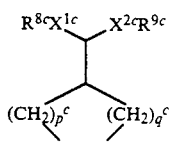

wherein $R^{8c}$, $R^{9c}$, $X^{1c}$ and $X^{2c}$ are as defined above, $p^c$ is 0, 1 or 2 and $q^c$ is 0, 1 or 2, with the proviso that the sum of $p^c$ and $q^c$ is 1, 2 or 3, with the proviso that if $X^{1c}$ and $X^{2c}$ are $CH_2$ then $R^{8c}$ and $R^{9c}$ taken together form a bridge $W^c$, wherein $W^c$ is as defined above;

$U^c$ is

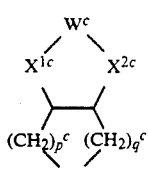

wherein $W^c$ is as defined above (except that $W^c$ may also be a methylene bridge when $X^{1c}$ and $X^{2c}$ are oxygen or sulfur), $X^{1c}$ and $X^{2c}$ are as defined above, $p^c$ is 0, 1 or 2, $q^c$ is 0, 1 or 2, with the proviso that the sum of $p^c$ and $q^c$ is 1 or 2, and with the proviso that if $p^c$ is 0, $X^{1c}$ must be $CH_2$;

$Y^c$ is

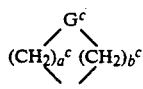

wherein $G^c$ is oxygen, sulfur or $CH_2$, $a^c$ is 2, 3 or 4 and $b^c$ is 1, 2, 3, 4 or 5, with the proviso that the sum of $a^c$ and $b^c$ is 5, 6 or 7 or $G^c$ is $CH_2$, $a^c$ is 0, 1, 2 or 3, $b^c$ is 0, 1, 2 or 3 with the proviso that the sum of $a^c$ and $b^c$ is 1, 2 or 3, with the proviso that the sum of $a^c$ and $b^c$ may be 1, 2 or 3 only if $R^{1c}$ is lower alkyl substituted with aralkylthio or aralkyloxy;

$D^c$ is

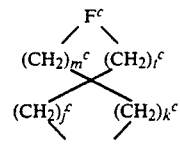

wherein $F^c$ is O or S, $j^c$ is 0, 1 or 2 and $k^c$ is 0, 1 or 2, with the proviso that the sum of $j^c$ and $k^c$ must be 1, 2 or 3, and $m^c$ is 1, 2 or 3 and $t^c$ is 1, 2 or 3, with the proviso that the sum of $m^c$ and $t^c$ must be 2, 3 or 4;

$E^c$ is

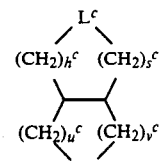

wherein $L^c$ is O or S, $u^c$ is 0, 1 or 2 and $v^c$ is 0, 1 or 2, with the proviso that the sum of $u^c$ and $v^c$ must be 1 or 2, and $h^c$ is 1 or 2 and $s^c$ is 1 or 2, with the proviso that the sum of $h^c$ and $s^c$ must be 2 or 3;

European Patent Application 0 079 522 published May 25, 1983 discloses N-carboxymethyl(amidino) lysyl-proline compounds which are said to be angiotensin converting enzyme inhibitors and have the formula where

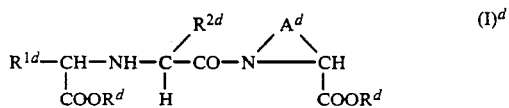

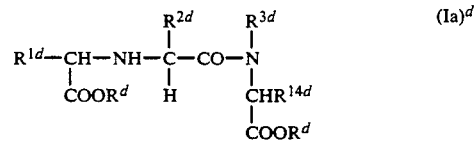

wherein:
$R^d$ and $R^{2d}$ are independently hydrogen; loweralkyl; aralkyl; or aryl;
$R^{1d}$ is hydrogen; branched or straight chain $C_{1-12}$ alkyl and alkenyl; $C_3$-$C_9$ cycloalkyl and benzofused alkyl; substituted loweralkyl where the substituents are halo, hydroxy loweralkoxy, aryloxy, amino, mono- or diloweralkylamino, acylamino, arylamino, guanidino, mercapto, loweralkylthio, arylthio, carboxy, carboxamido, or loweralkoxycarbonyl; aryl; substituted aryl where the substituents are loweralkyl, loweralkoxy, or halo; arloweralkyl; arloweralkenyl; heteroarloweralkyl; heteroarloweralkenyl; substituted arloweralkyl, substituted arloweralkenyl, substituted heteroarloweralkyl, or substituted heteroarloweralkenyl where the aryl and heteroaryl substituents are halo, dihalo, loweralkyl, hydroxy, loweralkoxy, amino, aminoloweralkyl, acylamino, mono- or diloweralkylamino, carboxyl, haloloweralkyl, nitro, cyano, or sulfonamido, and where the loweralkyl portion of arloweralkyl may be substituted by amino, acylamino, or hydroxyl;

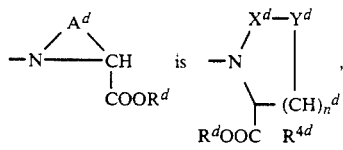 is 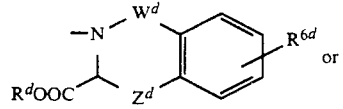,

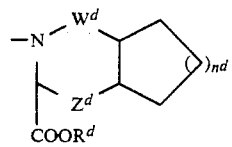

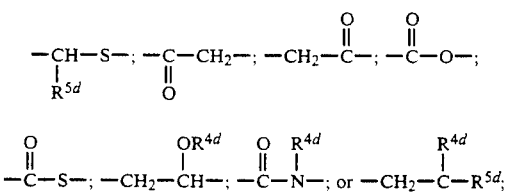

where:
$X^d$ and $Y^d$ taken together are $-CH_2-CH_2-$:

$R^{4d}$ is hydrogen; loweralkyl; aryl; substituted aryl;
$R^{5d}$ is hydrogen; loweralkyl; aryl or substituted aryl;
$n^d$ is 1 to 3;
$W^d$ is absent; $-CH_2-$;

or $-\overset{O}{\underset{\|}{C}}-$;

$Z^d$ is $-(CH_2)_{m^d}$, where $m^d$ is 0 to 2, provided that $m^d$ may not be 0 and $W^d$ may not be absent at the same time; and
$R^{6d}$ is hydrogen; loweralkyl; halo; or $OR^{4d}$;
$R^{2d}$ is $-(CH_2)_{r^d}-B^d-(CH_2)_{s^d}-NR^{7d}R^{15d}$ where $r^d$ and $s^d$ are independently 0 to 3;
$B^d$ is absent; $-O-$; $-S-$; or $-NR^{8d}$;
where $R^{8d}$ is hydrogen; loweralkyl; or alkanoyl; or aroyl; and
$R^{7d}$ is

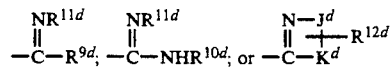

where
$R^{9d}$ is loweralkyl; aralkyl; aryl; heteroaryl; or heteroarloweralkyl and these groups substituted by hydroxy, lower alkoxy or halo; carboxyl; carboxamido; nitromethenyl.
$R^{10d}$ is hydrogen; loweralkyl; aryl; or amidino;
$R^{11d}$ is hydrogen; loweralkyl; cyano; amidino; aryl; aroyl; loweralkanoyl;

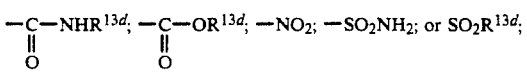

$R^{12d}$ is hydrogen; loweralkyl; halo; aralkyl; amino; cyano; mono- or diloweralkylamino; or $OR^{4d}$;
$R13d$ is hydrogen; loweralkyl; or aryl;
$R15d$ is hydrogen; lower alkyl; aralkyl; or aryl;

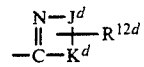

constitute a basic heterocycle of 5 or 6 atoms or benzofused analogs thereof and optionally containing 1-3 N atoms, an oxygen, a sulfur, an $S=O$, or an $SO_2$ group optionally substituted by amino, lower alkyl amino, diloweralkyl amino, lower alkoxy, or aralkyl groups;
$R^{3d}$ is $C_{3-8}$ cycloalkyl and benzofused $C_{3-8}$ cycloalkyl; perhydrobenzofused $C_{3-8}$ cycloalkyl; aryl; substituted aryl; heteraryl; substituted heteroaryl;
$R^{14d}$ is hydrogen or loweralkyl; and, a pharmaceutically acceptable salt thereof;

European Patent 79022 published May 18, 1983 discloses N-amino acyl-azabicyclooctane carboxylic acid derivatives which have the formula

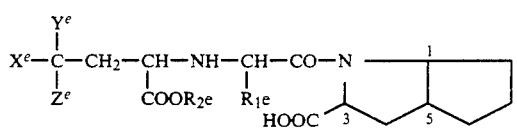

hydrogen atoms at ring positions 1 and 5 are cis to each other and the 3-carboxy group has the endo orientation;
$R_1^e$ is H, allyl, vinyl or the side chain of an optionally protected naturally occurring α-amino acid;
$R_2^e$ is H, 1-6C alkyl, 2-6C alkenyl or aryl(1-C alkyl);
$Y^e$ is H or OH and $Z^e$ is H, or $Y^e$ and $Z^e$ together oxygen;
$X^e$ is 1-6C alkyl, 2-6C alkenyl, 5-9C cycloalkyl, 6-12C aryl (optionally substituted by one to three 1-4C alkyl or alkoxy, OH, halo, nitro, amino (optionally substituted by one or two 1-4C alkyl), or methylenedioxy) or indol-3-yl);

European Patent 46953 published Mar. 10, 1982 discloses N-amino acyl-indoline and tetrahydro isoquinoline carboxylic acids which are angiotensin coverting enzyme inhibitors and have the formula

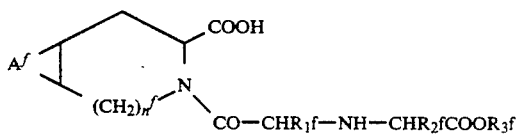

$n^f$ is 0 or 1;

is a benzene or cyclohexane ring:
$R_1^f$ and $R_2^f$ are each 1-6C alkyl, 2-6C alkenyl, 5-7C cycloalkyl, 5-7C cycloalkenyl, 7-12C cycloalkylalkyl, optionally partially hydrogenated 6-10C aryl, 7-14C aralkyl or 5-7 membered monocyclic or 8-10 membered bicyclic heterocyclyl containing 1 or 2 S or O and/or 1-4N atoms; all $R_1^f$ and $R_2{}^f$ groups are optionally substituted, $R_3{}^f$ is H, 1-6C alkyl, 2-6C alkenyl or 7-14C aralkyl.

The following Table III lists ACE inhibitors preferred for use in the combination of this invention.

TABLE III
PREFERRED ACE INHIBITORS $$R-\underset{R_1}{\underset{|}{CH}}-NH-\underset{R_2}{\underset{|}{CH}}-\underset{}{\overset{O}{\overset{\|}{C}}}-R^3$$
with COOR¹ on the first CH

| | R | R₁ | R₂ | R₃ |
|---|---|---|---|---|
| spirapril | C₆H₅CH₂CH₂— | Et | CH₃ | (spiro-dithiolane-proline ring system) |
| enalapril | C₆H₅CH₂CH₂— | Et | CH₃ | prolyl |
| ramipril | C₆H₅CH₂CH₂— | Et | CH₃ | (bicyclic cyclopentane-fused proline) |
| perindopril | CH₃CH₂CH₂— | Et | CH₃ | (cyclohexane-fused proline) |
| indolapril | C₆H₅CH₂CH₂— | Et | CH₃ | (cyclohexane-fused proline) |
| lysinopril | C₆H₅CH₂CH₂— | H | NH₂(CH₂)₄— | prolyl |
| quinapril | C₆H₅CH₂CH₂— | Et | CH₃ | (tetrahydroisoquinoline carboxylic acid) |
| pentopril (NH═CH₂) | CH₃ | Et | CH₃ | (indane-fused proline) |
| cliazapril | C₆H₅CH₂CH₂— | H | $\underset{R_2}{\underset{|}{CH}}-\overset{O}{\overset{\|}{C}}-R_3=$ (bicyclic pyridazine-CO₂H system) | |

$$RS-CH_2-CH_2-\underset{CH_3}{\underset{|}{C}}-\overset{O}{\overset{\|}{C}}-R^2$$

| | R | R₂ |
|---|---|---|
| captopril | H | prolyl |

TABLE III-continued
PREFERRED ACE INHIBITORS

| | | |
|---|---|---|
| zofenopril | $C_6H_5CO-$ | ![structure with $SC_6H_5$ group, $-N-C-COOH$] |
| pivalopril | $(CH_3)_3C-\overset{O}{\underset{\|}{C}}-$ | ![cyclopentyl ring with $-N-CH_2-COOH$] |

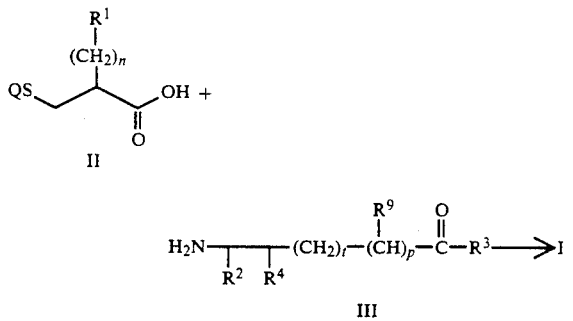

| | R | $R^1$ | $R^2$ |
|---|---|---|---|
| fosinopril | $C_6H_5-(CH_2)_4-$ | $\begin{array}{c}(CH_3)_2\\ \|\\ CH\\ \|\\ -CH-O-\underset{\underset{O}{\|\|}}{C}-CH_2CH_3\end{array}$ | $C_6H_5-$ |

Compounds of the present invention can be made by methods well known to those skilled in the art. A typical general procedure is to combine a propionic acid, II, with an amino ester or amino amide, III, under typical peptide coupling conditions, using, for example, a coupling agent such as 1-(3-dimethylaminopropyl)-3-ethylcarbodiimide hydrochloride (EDC):

$$QS-\underset{II}{\overset{\begin{array}{c}R^1\\ \|\\ (CH_2)_n\end{array}}{\diagdown}}\!\!\!\!\diagup\!\!\overset{O}{\underset{\|}{C}}-OH\ +$$

$$H_2N-\underset{R^2}{\overset{\|}{C}}-\underset{R^4}{\overset{\|}{C}}-(CH_2)_t-(CH)_p-\overset{\overset{R^9}{\|}}{\underset{\|}{C}}-R^3 \longrightarrow I$$

III

Alternatively, the propionic acid (II) can be converted by known methods (e.g. treatment with thionyl chloride) to the corresponding acid chloride (IV), and the acid chloride can be reacted with the amino acid, amino ester or amino amide in the presence of a base such as triethylamine to obtain a compound of formula I:

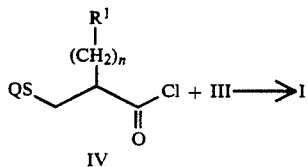

In the reaction schemes above, Q is typically acetyl or benzoyl and $R^3$ is typically alkoxy or benzyloxy. To obtain compounds of formula I wherein Q is hydrogen and $R^3$ is OH, the sulfur and hydroxy protecting groups can be removed by conventional means, e.g. removal of an acetyl or benzoyl group can be accomplished by treating with sodium hydroxide, then acidifying with HCl.

For compounds of formula III wherein $R^4$ is hydroxy, it may be desirable to protect such a group during the reaction, e.g. with a t-butoxycarbonyl or benzyloxycarbonyl group.

Compounds of formula II-IV are known in the art or can be prepared by methods well known in the art.

We have found that the novel compounds of the present invention are effective in treating cardiovascular disorders such as congestive heart failure, edema, renal insufficiency and various types of hypertension, particularly volume expanded hypertension. These novel compounds enhance both the magnitude and duration of the antihypertensive and natriuretic effects of endogenous ANF. Administration of a combination of a mercapto-acylamino acid and an ACE inhibitor provides an antihypertensive and anti-congestive heart failure effect greater than either the mercapto-acylamino acid or ACE inhibitor alone. Administration of a combination of a mercapto-acylamino acid of formula I and an exogenous ANF or ACE inhibitor is therefore particularly useful in treating hypertension or congestive heart failure.

In addition to the compound aspect, the present invention therefore also relates to treating cardiovascular disorders with a mercapto-acylamino acid of formula I or with a mercapto-acylamino acid of formula I in combination with an ANF or an ACE inhibitor, which methods comprise administering to a mammal in need of such treatment an amount of the mercapto-acylamino acid effective to treat hypertension or congestive heart failure or an amount of a combination of a mercapto-acylamino acid and ANF or ACE inhibitor effective to treat hypertension or congestive heart failure. The drug or combination of drugs is preferably administered in a pharmaceutically acceptable carrier, e.g. for oral or parenteral administration. The combinations of drugs may be co-administered in a single composition, or components of the combination therapy may be administered separately. Where the components are administered separately, any convenient combination of dosage forms may be used, e.g. oral mercapto-acylamino acid/oral ANF, oral mercaptoacylamino acid/parenteral ACE inhibitor, parenteral mercapto-acylamino acid/oral ANF, parenteral mercapto-acylamino acid/parenteral ACE inhibitor.

When the components of a combination of a mercapto-acylamino acid and an ANF are administered separately, it is preferred that the mercapto-acylamino acid be administered first.

The present invention also relates to a pharmaceutical composition comprising a mercapto-acylamino acid for use in treating hypertension or congestive heart failure, to a pharmaceutical composition comprising both a mercapto-acylamino acid and an ANF and to a pharmaceutical composition comprising both a mercapto-acylamino acid and an ACE inhibitor.

The antihypertensive effect of mercapto-acylamino acids was determined according to the following procedure:

Male Sprague Dawley rats weighing 100–150 g were anesthetized with ether and the right kidney was removed. Three pellets containing DOC acetate (desoxycorticosterone acetate, DOCA, 25 mg/pellet) were implanted subcutaneously. Animals recovered from surgery, were maintained on normal rat chow and were allowed free access to a fluid of 1% NaCl and 0.2% KCl instead of tap water for a period of 17–30 days. This procedure results in a sustained elevation in blood pressure and is a slight modification of published procedures (e.g. Brock et al., 1982) that have been used to produce DOCA salt hypertension in the rat.

On the day of study, animals were again anesthetized with ether and the caudal artery was cannulated for blood pressure measurement. Patency of the caudal artery cannula was maintained with a continuous infusion of dextrose in water at a rate of 0.2 ml/hr. Animals were placed into restraining cages where they recovered consciousness. Blood pressure was measured from caudal artery catheter using a Statham pressure transducer attached to a Beckman oscillographic recorder. In addition, a cardiovascular monitoring device (Buxco Electronics, Inc.) and a digital computer were used to calculate average blood pressures.

After an equilibration period of at least 1.5 hr., animals were dosed subcutaneously (1 ml/kg) with vehicle (methylcellulose, hereinafter MC) or mercapto-acylamino acid and blood pressure was monitored for the next 4 hours.

A similar procedure can be used to determine the effect of mercaptoacylamino acids in combination with ACE inhibitors.

The antihypertensive effect of mercapto-acylamino acids in combination with ANF can be determined according to the following procedures:

Male spontaneously hypertensive rats (SHR), 16–18 weeks old, 270–350 g, are anesthetized with ether and the abdominal aorta is cannulated through the tail artery. The animals are then placed into restrainers to recover from anesthesia (in less than 10 min.) and remain inside throughout the experiments. Through a pressure transducer (Gould P23 series) analog blood pressure signals are registered on a Beckman 612 recorder. A Buxco digital computer is used to obtain mean arterial pressures. Patency of the arterial cannula is maintained with a continuous infusion of 5% dextrose at 0.2 ml/hr. Animals are allowed a 90-min equilibration period. The animals first undergo a challenge with an ANF such as atriopeptin II (AP II) or AP28 30 )g/kg iv and at the end of 60 min. are treated with drug vehicle or a mercapto-acylamino acid subcutaneously. A second ANF challenge is administered 15 min. later and blood pressure is monitored for the next 90 min.

The antihypertensive effect in SHR of mercapto-acylamino acids and ACE inhibitors, alone and in combination, can be determined as follows:

Animals are prepared for blood pressure measurement as described above. After stabilization, animals are dosed subcutaneously or orally with test drugs or placebo and blood pressure is monitored for the next 4 hr.

The compounds having structural formula I have also been found to inhibit the activity of enzymes designated enkephalinases. The compounds are particularly useful for the inhibition of enkephalinase A, which is derived from the striata of both rats and humans. In in vitro tests, using test procedures for enkephalinase A inhibition well known to those skilled in the art, selected compounds having structural formula I have been found to inhibit the activity of the aforementioned enzyme. Therefore, the present invention also relates to a method of inhibiting the action of enkephalinases in a mammal thereby to elicit an analgesic effect with a compound of formula I, and to analgesic pharmaceutical compositions comprising compounds of formula I.

The compositions of this invention comprise a mercapto-acylamino acid or a mercaptoacylamino acid and an ANF or a mercapto-acylamino acid and an ACE inhibitor in combination with a pharmaceutically acceptable carrier for administration to mammals. A variety of pharmaceutical forms is suitable, preferably for oral or parenteral administration, although mechanical delivery systems such as transdermal dosage forms are also contemplated.

The daily dose of the compound or combinations of this invention for treatment of hypertension or congestive heart failure is as follows: for mercaptoacylamino acids alone the typical dosage is 1 to 100 mg/kg of mammalian weight per day administered in single or divided dosages; for the combination of mercapto-acylamino acid and an ANF, the typical dosage is 1 to 100 mg of mercapto-acylamino acid/kg mammalian weight per day in single or divided dosages plus 0.001 to 0.1 mg ANF/kg of mammalian weight per day, in single or divided dosages, and for the combination of mercapto-acylamino acid and an ACE inhibitor, the typical dosage is 1 to 100 mg of mercapto-acylamino acid/kg mammalian weight per day in single or divided dosages plus 0.1 to 30 mg ACE inhibitor/kg of mammalian weight per day in single or divided dosages. The exact dose of any component or combination to be administered is determined by the attending clinician and is dependent on the potency of the compound administered, the age, weight, condition and response of the patient.

Generally, in treating humans having hypertension or congestive heart failure, the compounds or combinations of this invention may be administered to patients in a dosage range as follows: for treatment with mercaptoacylamino acids alone, about 10 to about 500 mg per dose given 1 to 4 times a day, giving a total daily dose of about 10 to 2000 mg per day; for the combination of mercaptoacylamino acid and ANF, about 10 to about 500 mg mercapto-acylamino acid per dose given 1 to 4 times a day and about 0.001 to about 1 mg ANF given 1 to 6 times a day (total daily dosage range of 10 to 2000 mg day and .001 to 6 mg/day, respectively); and for the combination of a mercapto-acylamino acid and an ACE inhibitor, about 10 to about 500 mg mercaptoacylamino acid per dose given 1 to 4 times a day and about 5 to about 50 mg ACE inhibitor given 1 to 3 times a day (total daily dosage range of 10 to 2000 mg/day and 5 to 150 mg/day, respectively). Where the components of a combination are administered separately, the number of doses of each component given per day may not necessarily be the same, e.g. where one component may have a greater duration of activity, and will therefore need to be administered less frequently.

To produce an analgesic effect, compounds of this invention will be administered in a dosage range of from about 1 to about 100 mg/kg. The doses are to be administered at intervals of from 3 to 8 hours. However, the quantity and frequency of dosage will depend upon such factors as the severity of the pain, the general physical condition of the patient, the age and weight of the patient, and other factors recognized by the skilled clinician.

Typical oral formulations include tablets, capsules, syrups, elixirs and suspensions. Typical injectable formulations include solutions and suspensions.

The typical acceptable pharmaceutical carriers for use in the formulations described above are exemplified by: sugars such as lactose, sucrose, mannitol and sorbitol, starches such as cornstarch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone, polyvinyl alcohol; stearic acid; alkaline earth metal stearates such as magnesium stearate and calcium stearate, stearic acid, vegetable oils such as peanut oil, cottonseed oil, sesame oil, olive oil and corn oil; non-ionic, cationic and anionic surfactants; ethylene gylcol polymers; betacyclodextrin; fatty alcohols and hydrolyzed cereal solids; as well as other non-toxic compatible fillers, binders, disintegrants, buffes, perservatives, antioxidants, lubricants, flavoring agents, and the like commonly used in pharmaceutical formulations.

Since the present invention relates to treatment of hypertension or congestive heart failure with a combination of active ingredients wherein said active ingredients may be administered separately, the invention also relates to combining separate pharmaceutical compositions in kit form. That is, two kits are contemplated, each combining two separate units: a mecapto-acylamino acid pharmaceutical composition and an ANF pharmaceutical composition in one kit and a mercaptoacylamino acid pharmaceutical composition and an ACE inhibitor pharmaceutical composition in a second kit. The kit form is particularly advantageous when the separate components must be administered in different dosage forms (e.g. oral and parenteral) or are administered at different dosage intervals.

Following are examples of procedures for preparing compounds of formula I.

PREPARATION 1

(S)-ISOSERINE BENZYL ESTER, HYDROCHLORIDE

At 0°–5°, add thionyl chloride (11.0 ml) dropwise to N-(4-methoxybenzyloxycarbonyl)-(S)-isoserine (10.0 g) in benzyl alcohol (100 ml), warm the mixture to room temperature, and stir for 20 hours. Pour the reaction mixture into diethyl ether (300 ml) and filter the solid. Wash the solid with diethyl ether and dry in vacuo to give the title compound, a tan solid, m.p. 127°–130° C., $[\alpha]_D^{26} = -18.6°$ (MeOH).

PREPARATION 2

(S)-ISOSERINE ETHYL ESTER, HYDROCHLORIDE

At 0°–5°, add thionyl chloride (2.80 ml) dropwise to N-(4-methoxybenzyloxycarbonyl)-(S)-isoserine (5.0 g) in absolute ethanol (100 ml). Heat the mixture under reflux for 1 hour and stir for 20 hours at room temperature. Concentrate the reaction mixture in vacuo and pour the reaction mixture into diethyl ether (300 ml), and filter the solid. Wash the solid with diethyl ether and dry in vacuo to give the title compound, an amber oil, $[\alpha]_D^{26} = -19.8°$ (MeOH).

In a similar manner, convert N-(4-methoxybenzyloxycarbonyl)-(R)-isoserine to (R)-isoserine ethyl ester hydrochloride, a light brown oil, $[\alpha]_D^{26} = +25.0°$ (MeOH).

In a similar manner, convert N-(4-methoxybenzyloxycarbonyl)-(R)-isoserine to (R)-isoserine methyl ester hydrochloride, a light brown oil, $[\alpha]_D^{26} = +27.2°$ (MeOH).

PREPARATION 2A

(S)-ISOSERINE ETHYL ESTER. p-TOLUENESULFONATE

Heat (S)-isoserine (30.0 g) and p-toluenesulfonic acid (57.0 g) in absolute ethanol (300 ml) under reflux for 3.5 hours. Concentrate the mixture in vacuo. Add absolute ethanol (100 ml) and concentrate the mixture in vacuo (twice). Triturate the thick oily residue with diethyl ether and filter to obtain the title compound as a white solid, $[\alpha]_D^{26} = -13.2°$ (MeOH).

PREPARATION 3

α-PHENYL-β-ALANINE ETHYL ESTER

Method A

Hydrogenate ethyl phenylcyanoacetate (4.0 g, 21 mmol) in EtOH (75 ml) over $PtO_2$ (2.0 g) at 3 atm. for 3 hr. Concentrate and chromatograph over silica, eluting with 2% $MeOH/Et_2O$ to obtain the title compound as an oil.

Method B

Step 1: Ethyl α-hydroxy-β-nitro-α-phenylpropionate. Combine ethyl benzoylformate (7.1 g, 40 mmol), nitromethane (4.9 g, 80 mmol), and triethylamine (0.8 g, 8 mmol). After 5 days, concentrate and distill to obtain the hydroxyester, b.p. 125°–40° C./0.5 mm.

Step 2: Ethyl β-amino-α-hydroxy-α-phenyl-propionate. Hydrogenate the above hydroxyester as in Method A to obtain, after filtration and concentration, the aminoester as an oil.

Step 3: Ethyl 5-phenyloxazolidin-2-one-5-carboxylate. Combine the above aminoester (1.0 g, 4.1 mmol) with 1,1-carbonyldiimidazole (0.72 g, 4.5 mmol) and triethylamine (0.40 g, 4.1 mmol) in $CH_3CN$ (60 ml). After 18 hr., concentrate and partition between EtOAc and 1N HCl. Dry and concentrate the EtOAc to give a solid. Recrystallize from $CH_2Cl_2$-hexane to obtain the ester as a white solid, m.p. 114°–7° C.

Step 4: Ethyl β-amino-α-phenylpropionate hydrochloride (α-Phenyl-β-alanine ethyl ester, hydrochloride). Hydrogenate the above ester (0.73 g, 3.1 mmol) in EtOH (50 ml) for 1 hr. at 3 atm. with 20% Pd(OH)$_2$/C. Filter, concentrate, and treat the residual oil with HCl/Et$_2$O to obtain the title salt as a white solid, m.p. 156°–9° C.

PREPARATION 4

β-(2-NAPHTHYL)-β-ALANINE METHYL ESTER, HYDROCHLORIDE

Mix equimolar amounts of 2-naphthaldehyde and malonic acid in 95% EtOH containing two equivalents of ammonium acetate and reflux the reaction overnight. Cool the reaction mixture externally with ice water and collect the precipitate (β-(2-naphthyl)-β-alanine). Suspend the precipitate in dry acidified MeOH and again reflux overnight. Cool and collect the title compound, m.p. 188°–190° C.

PREPARATION 5

β-(PHENYL)-ISOSERINE METHYL ESTER, HYDROCHLORIDE

Mix equimolar amounts of benzaldehyde and methyl chloroacetate and cool to 0° C. Add a slurry of an equivalent of K-OtBu in dry t-BuOH over 1 hr. Stir and allow to warm to room temperature overnight. Concentrate in vacuo, extract the residue with Et$_2$O, and remove the volatiles to give a pale oil. Dissolve this oil in cold EtOH and add KOH in EtOH. Cool the mixture overnight, collect the precipitate, wash with EtOH, then Et$_2$O, and dry to obtain the potassium salt of 3-phenyl glycidic acid. Dissolve this in conc. NH$_4$OH and stir at room temperature for a week. Concentrate the solvent, dissolve the residue in dry acidified MeOH and reflux overnight, then concentrate and crystallize the residue from MeOH/Et$_2$O to obtain the title compound, m.p. 153°–156° C.

PREPARATION 5A

β-(3-THIENYL)-ISOSERINE METHYL ESTER, HYDROCHLORIDE

In a manner similar to that described in Preparation 5, combine thiophene 3-carboxaldehyde with ethyl chloroacetate to obtain the title compound.

PREPARATION 6

β-(p-BIPHENYLYL)-β-ALANINE METHYL ESTER HYDROCHLORIDE

In a manner similar to that described in Preparation 4, suspend equimolar amounts of p-biphenyl-carboxaldehyde and malonic acid in 95% EtOH containing 2 equivalents of NH$_4$OAc and reflux the reaction 36 hrs. Cool the reaction mixture externally with ice water and collect the precipitate (β-(p-biphenylyl)-β-alanine, m.p. 222°–224° C.). Suspend in dry acidified MeOH and reflux overnight. After cooling, collect the title compound as a precipitate, m.p. 208°–210° C.

PREPARATION 7

β-(3-THIENYL)-β-ALANINE METHYL ESTER, HYDROCHLORIDE

In a manner similar to that described in Preparation 4, suspend equimolar amounts of thiophene-3-carboxaldehyde and malonic acid in 95% EtOH containing 2 equivalents of NH$_4$OAc and reflux the reaction overnight. Cool the reaction mixture externally with ice water and collect the precipitate (β-(3-thienyl)-β-alanine). Suspend the precipitate in dry acidified MeOH and reflux overnight. Cool, concentrate and crystallize the residue from Et$_2$O to obtain the title compound, m.p. 121°–123° C.

PREPARATION 8

β-PHENYL-β-ALANINE METHYL ESTER, HYDROCHLORIDE

Suspend β-phenyl-β-alanine in dry acidified MeOH and reflux overnight. Cool, concentrate and crystallize to obtain the title compound, m.p. 142°–144° C.

PREPARATION 9

4-AMINO-2(S)-HYDROXYBUTYRIC ACID ETHYL ESTER, HYDROCHLORIDE

Add 4-benzyloxycarbonylamino-2(S)-hydroxybutyric acid (2.57 g) to absolute ethanol (30 ml) containing thionyl chloride (2.0 ml) and heat the resulting mixture under reflux for 20 hours. Cool, filter and concentrate the reaction mixture in vacuo to give a pale yellow oil. Chromatograph this oil on a column of silica gel (500 ml) using ethyl acetate as eluant to obtain a yellow oil, $[\alpha]_D^{26} = +0.4°$ (MeOH). Hydrogenate the product (1.4 g) in absolute ethanol (50 ml) containing 10% Pd/C (0.50 g) at 50 psi for 2 hours. Filter the mixture and concentrate the mixture in vacuo to give the title compound as an oil.

PREPARATION 10

(S)-O-METHYL ISOSERINE METHYL ESTER, HYDROCHLORIDE

Dissolve (S)-isoserine in dry MeOH saturated with HCl and reflux with the exclusion of moisture for 24 hours. Cool and remove the volatiles. Dissolve the residual waxy solid (mp 90°–95° C.) containing (S)-isoserine methyl ester in DMF/methylene chloride, adjust the pH to around eight with triethylamine, and react this with a slight molar excess of di-t-butyl dicarbonate at room temperature overnight. After this period, remove the volatiles and partition the residue between ethyl acetate and aqueous citric acid solution. Extract the aqueous layer with fresh ethyl acetate and evaporate the combined orgaic layers to give N-Boc-(S)-isoserine methyl ester, an oil. Dissolve this in dimethoxyethane, add a two-fold molar excess each of iodomethane and silver(1) oxide, and reflux in an inert atmosphere. Additional small aliquots of Ag$_2$O and CH$_3$I may be added at eight hour intervals as required for a total reaction time of 24 hours. Cool the reaction, filter the residue through a Soxhlett thimble and extract with ethyl acetate to give N-Boc-O-methyl-(S)-isoserine, methyl ester. Treat this with HCl in dioxane/methylene chloride at room temperature for two hours, remove the volatiles, and crystallize from methanol/ether to obtain the title compound.

EXAMPLE 1

N-[2(R,S)-ACETYLTHIOMETHYL-3-PHENYL-PROPANOYL]-(S)-ISOSERINE BENZYL ESTER

Add 2(R,S)-acetylthiomethyl-3-phenylpropionic acid (0.59 g) to (S)-isoserine benzyl ester, hydrochloride (0.578 g), 1-(3-dimethylaminopropyl)-3-ethylcarbodiimide hydrochloride (EDC) (0.53 g), 1-hydroxybenzotriazole (HOBT) (0.37 g) and N-methylmorpholine (0.80 ml) in dimethylformamide (DMF) (10 ml), and stir the resulting mixture for 20 hours. Concentrate the reaction mixture in vacuo and partition the residue between dichloromethane/water. Concentrate the dried (MgSO$_4$) dichloromethane solution in vacuo. Chromatograph the resulting residue on a column of silica gel (1 L) using chloroform:methanol 19.5:1 as eluant to give the title compound, a colorless oil, $[\alpha]_D^{26} = +12.3°$ (MeOH).

In a similar manner, substitute (R)-isoserine methyl ester, hydrochloride to obtain N-[2-(R,S)-acetylthiomethyl-3-phenylpropanoyl]-(R)-isoserine methyl ester, a colorless oil, $[\alpha]_D^{26} = -16.0°$ (MeOH).

EXAMPLE 2

N-[2(R,S)-MERCAPTOMETHYL-3-PHENYL-PROPANOYL]-(S)-ISOSERINE

Under a nitrogen atmosphere, at 0°-5° C., treat the product of Example 1 (0.63 g) in methanol (40 ml) with 1N NaOH (4.70 ml) and then keep the reaction mixture at 0°-5° C. for 20 hours. Add additional 1N NaOH (1.6 ml) and keep at 0.5° C. for 24 hours. Concentrate the mixture under nitrogen, dilute with water, and extract with ethyl acetate. Make the basic solution acidic with 1N HCl and extract with ethyl acetate. Concentrate the dried (MgSO$_4$) ethyl acetate in vacuo to give the title compound, a colorless viscous oil, $[\alpha]_D^{26} = +6.6°$ (MeOH).

In a similar manner substitute N-[2(R,S)-acetylthiomethyl3-phenylpropanoyl]-(R)-isoserine methyl ester to obtain N-[2(R,S)-mercaptomethyl-3-phenylpropionyl]-(R)-isoserine, a colorless viscous oil, $[\alpha]_D^{26} = -3.3°$ (MeOH).

EXAMPLE 3

N-[2(S)-ACETYLTHIOMETHYL-3-(2-METHYL-PHENYL)-PROPANOYL]-(S)-ISOSERINE ETHYL ESTER

Combine 2(S)-acetylthiomethyl-3-(2-methylphenyl)-propionic acid (1.65 g) and (S)-isoserine ethyl ester hydrochloride (1.10 g), EDC (1.51 g), HOBT (0.99 g) and N-methylmorpholine (1.50 ml) in DMF (10 ml), and stir the resulting mixture for 20 hours. Concentrate the reaction mixture in vacuo and partition the residue between dichloromethane/water. Concentrate the dried (MgSO$_4$) dichloromethane solution in vacuo. Chromatograph the resulting residue on a column of flash silica gel (300 ml) using ethyl acetate:hexane (1:3); ethyl acetate; ethyl acetate:methanol (9:1) as eluant to give the title compound, a colorless oil, $[\alpha]_D^{26} = 0°$ (MeOH).

Alternatively, (S)-isoserine ethyl ester, p-toluenesulfonate may be used in place of the hydrochloride to prepare the title compound.

In a similar manner, substitute (R)-isoserine ethyl ester to obtain N-[2(S)-acetylthiomethyl-3-(2-methylphenyl)propanoyl]-(R)-isoserine ethyl ester, a colorless oil, $[\alpha]_D^{26} = -25.4°$ (MeOH).

EXAMPLE 4

N-(2-ACETYLTHIOMETHYL-3-PHENYL-PROPANOYL)-β-(2-NAPHTHYL)-β-ALANINE METHYL ESTER

Mix equimolar parts of β-(2-naphthyl)-β-alanine methyl ester, hydrochloride and 2-acetylthiomethyl-3-phenylpropanoic acid with 1.2 equivalents each of EDC, triethylamine and HOBT in DMF and stir overnight. Evaporate the solvent, partition between EtOAc and water, and concentrate the organic layer. Separate on silica using ether/hexane and crystallize from acetone/hexane to obtain the title compound, m.p. 133°–135° C.

Use a procedure similar to that described in Example 4 to obtain the following compounds of formula I wherein n is 1 and p is zero:

| | AMINO ACID ESTER | | | | PROPANOIC ACID | | |
|---|---|---|---|---|---|---|---|
| Ex | R$^2$ | R$^4$ | t | R$^3$ | Q | R$^1$ | Characterizing Data |
| 5 | 4-PhC$_6$H$_4$— | H | 0 | OMe | Ac | Ph | m.p. 100–104° C.; FAB-MS: 476 (M + 1) |
| 6 | Ph | OH | 0 | OMe | Ac | Ph | Isomer A: m.p. 108–110° C. Isomer B: m.p. 128–129° C. |
| 7 | H | OH | 1 | OMe | Ac | Ph | FAB-MS: 354 (M + 1) |
| 8 | 3-The | H | 0 | OMe | Ac | Ph | FAB-MS: 406 (M + 1); Elemental Analysis: C(59.24) 59.76; H(5.72) 5.81; N(3.45) 7.52 |
| 9 | 2-The | H | 0 | OEt | Bz | Ph | FAB-MS: 482 (M + 1) |
| 10 | Ph | OH | 0 | OMe | Ac | o-Tol | Isomer A: m.p. 140–144° C. Isomer B: m.p. 136–137° C. |
| 11 | H | OMe | 0 | OMe | Ac | o-Tol | m.p. 78–82° C. |
| 12 | H | Benzyl | 0 | OEt | Ac | o-Tol | FAB-MS: 442 (M + 1); Elemental Analysis: C(68.00) 68.18; H(7.07) 6.99; N(3.17) 3.32 |
| 13 | 3-The | H | 0 | OMe | Ac | o-Tol | m.p. 75–76° C.; FAB-MS: 420 (M + 1) |
| 22 | 3-The | OH | 0 | OMe | Ac | Ph | Isomer A: m.p. 117–120° C. Isomer B: m.p. 120–122° C. |

(Ph = phenyl; Bz = benzoyl; o-Tol = o-tolyl; The = thienyl)

EXAMPLE 14

N-(2-MERCAPTOMETHYL-3-PHENYL-PROPANOYL)-β-(2-NAPHTHYL)-β-ALANINE and the METHYL ESTER THEREOF Hydrolyze the product of Example 4 in aqueous alcoholic K$_2$CO$_3$. Evaporate the solvent and treat the residue with zinc and aqueous acid. Extract with ethyl acetate and separate by reverse phase chromatography to obtain the title compounds, FAB-MS: 394 (M+1) and FAB-MS: 408 (M+1), respectively.

In a manner similar to that described in Example 14, treat the products of Examples 5–13 to obtain the corresponding mercaptoacyl-substituted amino acids:

| Example | Starting Material | Characterizing Data |
|---|---|---|
| 15 | Ex. 5 | FAB-MS: 420 (M + 1) |
| 16A | Ex. 6A | FAB-MS: 360 (M + 1) |
| 16B | Ex. 6B | FAB-MS: 360 (M + 1) |

-continued

| Example | Starting Material | Characterizing Data |
|---------|-------------------|---------------------|
| 17 | Ex. 7 | FAB-MS: 298 (M + 1) |
| 18 | Ex. 8 | FAB-MS: 350 (M + 1) |
| 19 | Ex. 13 | m.p. 45-55° C. |

EXAMPLE 20

N-(2-MERCAPTOMETHYL-3-PHENYL-PROPANOYL)-α-PHENYL-β-ALANINE

Combine the product of Preparation 3 (0.94 g, 4.9 mmol) with triethylamine (0.54 g, 5.4 mmol) in 2:1 $CH_3CN/H_2O$ (60 ml). Add 2-(acetylthio)-3-phenylpropionyl chloride (1.37 g, 5.4 mmol). Stir 1 hr., add 1N HCl, and extract with $Et_2O$. Dry, concentrate, and chromatograph the resulting oil on silica, eluting with 4:6 $Et_2O$-hexane, to obtain the amide as a foam.

Dissolve the above ester in MeOH (6 ml) and add 1.0N NaOH (3.0 ml). Stir 18 hr., concentrate, add 1.0N HCl (3.0 ml), and extract with EtOAc. Dry concentrate to obtain the title compound, a mixture of diastereomers, as a colorless foam, FAB-MS: $M+1=344$.

EXAMPLE 21

N-(2(S)-ACETYLTHIOMETHYL-3-(2-METHYLPHENYL)-PROPANOYL)-α-PHENYL-β-ALANINE ETHYL ESTER

Combine α-phenyl-β-alanine ethyl ester, hydrochloride (0.40 g, 1.7 mmol) with 2(S)-acetylthiomethyl-3-(2-methylphenyl)propionic acid (0.44 g, 1.77 mmol), HOBT (0.26 g, 1.7 mmol) and triethylamine (0.25 g, 2.6 mmol) in 15 ml DMF. Add EDC (0.32 g, 1.7 mmol), stir 18 hr., partion with EtOAc-water, and wash with 1N HCl, then $NaHCO_3$. Chromatograph on silica, eluting with 1:1 $Et_2O$-hexane, to obtain the title compound, a 1:1 mixture of diastereomers, as an oil, $[\alpha]_D^{26} = -19.9°$ (EtOH).

EXAMPLES 23-25

In a manner similar to that described in Example 20, treat the products of Examples 10, 11 and 21 to obtain the corresponding mercaptoacyl substituted amino acids:

| Example | Starting Material | Characterizing Data |
|---------|-------------------|---------------------|
| 23 | Ex. 10 | m.p. 55-60° C. |
| 24 | Ex. 11 | m.p. 90-95° C. |
| 25 | Ex. 12 | $[\alpha]_D^{26} = +40.2°$ (EtOH) |

EXAMPLE 26

4-[2(S)-ACETYLTHIOMETHYL-3-(2-METHYLPHENYL)PROPIONYLAMINO]-2-(S)-HYDROXYBUTYRIC ACID ETHYL ESTER

Using a procedure similar to that described in Example 3, combine 2(S)-acetylthiomethyl-3-(2-methylphenyl)propionic acid (1.18 g), the product of Preparation 9 (0.85 g), EDC (1.09 g), HOBT (0.72 g) and N-methylmorpholine (0.52 ml) in DMF (20 ml). Chromatograph the residue on silica gel using hexane:ethyl acetate 3:2 as eluant to obtain the title compound as a white solid, m.p. 48°-52° C., $[\alpha]_D^{26} = -25.9°$ (MeOH).

EXAMPLES 27-29

In a manner similar to that described in Example 2, hydrolyze the products of Examples 3, 22 and 26 to obtain the corresponding mercaptoacyl amino acids:

| Example | Starting Material | Characterizing Data |
|---------|-------------------|---------------------|
| 27a | Ex. 3 - (R)-ester | $[\alpha]_D^{26} = +42.4°$ (MeOH) |
| 27b | Ex. 3 - (S)-ester | m.p. 99-100° C.; $[\alpha]_D^{26} = +62.6°$ (MeOH) |
| 28 | Ex. 22 | FAB-MS: M + 1 = 366 |
| 29 | Ex. 26 | $[\alpha]_D^{26} = +39.7°$ (MeOH) |

The following formulations exemplify some of the dosage forms of the compositions of this invention. In each, the term "active compound" designates a compound of formula I, preferably N-[2(S)-mercaptomethyl-3-(2-methylphenyl)propanoyl]-(S)-isoserine. However, this compound may be replaced by equally effective amounts of other compounds of formula I.

Pharmaceutical Dosage Form Examples

Example A

| | Tablets | | |
|---|---|---|---|
| No. | Ingredient | mg/tablet | mg/tablet |
| 1 | Active Compound | 100 | 500 |
| 2 | Lactose USP | 122 | 113 |
| 3 | Corn Starch, Food Grade, as a 10% Paste in Purified Water | 30 | 40 |
| 4 | Corn Starch, Food Grade | 45 | 40 |
| 5 | Magnesium Stearate | 3 | 7 |
| | Total | 300 | 700 |

Method of Manufacture

Mix Items Nos. 1 and 2 in suitable mixer for 10-15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10-15 minutes. Add Item No. 5 and mix for 1-3 minutes. Compress the mixture to appropriate size and weigh on a suitable tablet machine.

Example B

| | Capsules | | |
|---|---|---|---|
| No. | Ingredient | mg/capsule | mg/capsule |
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
| | Total | 250 | 700 |

Method of Manufacture

Mix Item Nos. 1, 2 and 3 in a suitable blender for 10-15 minutes. Add Item No. 4 and mix for 1-3 minutes. Fill the mixture into suitable two-piece hard gelatin capsules on a suitable encapsulating machine.

Example C

| Parenteral Preparation | | |
|---|---|---|
| Ingredient | mg/vial | mg/vial |
| Active Compound Sterile Powder | 100 | 500 |

We claim:

1. A compound represented by the formula

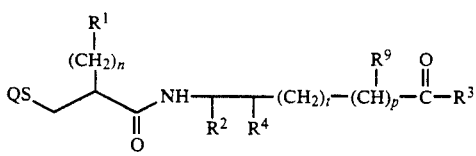

wherein

Q is hydrogen or $R^7CO-$;

$R^1$ is lower alkyl, cyclolower alkyl, aryl or heteroaryl;

$R^2$ is hydrogen; lower alkyl; cyclolower alkyl; lower alkyl substituted with hydroxy, lower alkoxy, mercapto, lower alkylthio, aryl or heteroaryl; aryl; or heteroaryl;

$R^3$ is $-OR^5$ or $-NR^5R^6$;

$R^4$ is lower alkoxy;

$R^9$ is $-(CH_2)_qR^8$;

$R^5$ and $R^6$ are independently selected from the group consisting of hydrogen, lower alkyl, hydroxy lower alkyl, lower alkoxy lower alkyl and aryl lower alkyl, or $R^5$ and $R^6$ together with the nitrogen to which they are attached form a 5–7 membered ring;

$R^7$ is hydrogen, lower alkyl, or aryl;

$R^8$ is hydrogen, hydroxy, lower alkoxy, mercapto, lower alkylthio, aryl or heteroaryl;

n is 1 or 2;

q is 0;

q is 0, 1 or 2; and t is 0;

or a pharmaceutically acceptable salt thereof.

2. A compound of claim 1 wherein Q is hydrogen or acyl.

3. A compound of claim 1 further characterized by $R^1$ being phenyl or lower alkyl substituted phenyl and n being 1.

4. A compound of claim 1, further characterized by $R^3$ being hydroxy or lower alkoxy.

5. A compound of claim 1 further characterized by $R^2$ being hydrogen or thienyl.

6. A compound of claim 1 selected from the group consisting of N-(S)-[3-mercapto-2-(2-methylbenzyl)propionyl](S)-2-methoxy-β-alanine and N-(S)-[3-acetylthio-2-(2-methylbenzyl)propionyl]-(S)-2-methoxy-β-alanine methyl ester.

7. A pharmaceutical composition comprising an effective amount of a compound of claim 1 in a pharmaceutically acceptable carrier.

8. A method of treating hypertension or congestive heart failure comprising administering a pharmaceutical composition of claim 7 to a mammal in need of such treatment.

9. A method of treating edema, renal insufficiency or pain comprising administering a pharmaceutical composition of claim 8 to a mammal in need of such treatment.

10. A method of potentiating atrial natriuretic factor comprising administering to a mammal in need of much treatment an effective amount of a compound having the structural formula

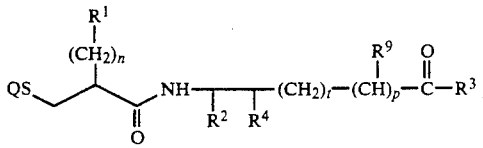

wherein

Q is hydrogen or $R^7CO-$;

$R^1$ is lower alkyl, cyclolower alkyl, aryl or heteroaryl;

$R^2$ is hydrogen; lower alkyl; cyclolower alkyl; lower alkyl substituted with hydroxy, lower alkoxy, mercapto, lower alkylthio, aryl or heteroaryl; aryl; or heteroaryl;

$R^3$ is $-OR^5$ or $-NR^5R^6$;

$R^4$ and $R^9$ are independently $-(CH_2)_qR^8$, provided that when $R^4$ and $R^9$ are both hydrogen, $R^2$ is biphenylyl, phenoxyphenyl, phenylthiophenyl, naphthyl, heteroaryl, or lower alkyl substituted with hydroxy, lower alkoxy, mercapto or lower alkylthio;

$R^5$ and $R^6$ are independently selected from the group consisting of hydrogen, lower alkyl, hydroxy lower alkyl, lower alkoxy lower alkyl and aryl lower alkyl, or $R^5$ and $R^6$ together with the nitrogen to which they are attached form a 5–7 membered ring;

$R^7$ is hydrogen, lower alkyl, or aryl;

$R^8$ is hydrogen, hydroxy, lower alkoxy, mercapto, lower alkylthio, aryl or heteroaryl;

n is 1 or 2;

p is 0 or 1;

q is 0, 1 or 2; and t is 0 or 1;

or a pharmaceutically acceptable salt thereof.

* * * * *

UNITED STATES PATENT AND TRADEMARK OFFICE
CERTIFICATE OF CORRECTION

PATENT NO. : 5,219,886

DATED : June 15, 1993

INVENTOR(S) : Elizabeth M. Smith, Philip M. DeCapite and Bernard R. Neustadt It is certified that error appears in the above-identified patent and that said Letters Patent is hereby corrected as shown below:

In column 27, line 35, delete "q is 0" and insert instead --p is 0--.

In column 28, line 10, delete "claim 8" and insert instead --claim 7--.

Signed and Sealed this

First Day of February, 1994

Attest:

BRUCE LEHMAN

Attesting Officer

Commissioner of Patents and Trademarks